(12) United States Patent  (10) Patent No.: US 8,292,867 B2
Vigmo  (45) Date of Patent: Oct. 23, 2012

(54) BELTED ABSORBENT ARTICLE

(75) Inventor: Terje Vigmo, Mölnlycke (SE)

(73) Assignee: SCA Hygiene Products AB, Göteborg (SE)

( * ) Notice: Subject to any disclaimer, the term of this patent is extended or adjusted under 35 U.S.C. 154(b) by 119 days.

(21) Appl. No.: 12/677,873

(22) PCT Filed: Oct. 10, 2007

(86) PCT No.: PCT/SE2007/050730
§ 371 (c)(1),
(2), (4) Date: Mar. 12, 2010

(87) PCT Pub. No.: WO2009/048360
PCT Pub. Date: Apr. 16, 2009

(65) Prior Publication Data
US 2010/0256588 A1   Oct. 7, 2010

(51) Int. Cl.
*A61F 13/15* (2006.01)
(52) U.S. Cl. ........ 604/389; 604/391; 604/392; 604/387; 604/390; 604/394; 604/396
(58) Field of Classification Search .................. 604/391, 604/392, 387, 390, 394, 396, 389
See application file for complete search history.

(56) References Cited

U.S. PATENT DOCUMENTS

| | | | |
|---|---|---|---|
| 5,374,262 A | 12/1994 | Keuhn, Jr. et al. | |
| 5,386,595 A | 2/1995 | Kuen et al. | |
| 5,423,789 A | 6/1995 | Kuen | |
| 5,722,968 A | 3/1998 | Datta et al. | |
| 5,749,866 A | 5/1998 | Roe et al. | |
| 2002/0052584 A1 | 5/2002 | Forgar | |
| 2002/0062118 A1* | 5/2002 | Almberg et al. | ............ 604/392 |
| 2003/0083634 A1 | 5/2003 | Fernfors | |
| 2006/0247598 A1 | 11/2006 | Roehrl et al. | |

FOREIGN PATENT DOCUMENTS

| | | |
|---|---|---|
| DE | 198 13 334 B4 | 9/1999 |
| EP | 0 605 012 A1 | 7/1994 |
| EP | 1 035 818 A1 | 9/2000 |
| FR | 2 586 558 A1 | 3/1987 |
| GB | 2 080 093 A | 2/1982 |
| JP | 4-96749 A | 3/1992 |
| JP | 6-218010 A | 8/1994 |
| JP | 7-439 A | 1/1995 |
| JP | 2003-528693 A | 9/2003 |
| WO | WO 99/27876 A1 | 6/1999 |
| WO | 01/74280 A1 | 10/2001 |

(Continued)

OTHER PUBLICATIONS

International Search Report in Application No. PCT/SE2007/050730 dated Jun. 24, 2008.

(Continued)

*Primary Examiner* — Jacqueline F. Stephens
(74) *Attorney, Agent, or Firm* — Buchanan Ingersoll & Rooney PC (57) ABSTRACT

An absorbent article has a belt and an absorbent structure. The absorbent structure is fastened to the belt via an article fastener having a form such that the article fastening means does not fold or bend upwards under the forces present when the diaper is assembled.

15 Claims, 6 Drawing Sheets

FOREIGN PATENT DOCUMENTS

| | | |
|---|---|---|
| WO | 02/05739 A1 | 1/2002 |
| WO | 02/22061 A1 | 3/2002 |
| WO | 03/017903 A1 | 3/2003 |
| WO | 03/017904 A1 | 3/2003 |
| WO | 2006/065177 A1 | 6/2006 |
| WO | 2007/149016 A1 | 12/2007 |
| WO | 2008/039112 A1 | 4/2008 |

OTHER PUBLICATIONS

Written Opinion of the International Searching Authority in Application No. PCT/SE2007/050730 dated Jun. 24, 2008.

International Preliminary Report on Patentability in Application No. PCT/SE2007/050730 dated Sep. 18, 2009.

Decision on Grant Patent for Invention issued in corresponding RU 2010118317 dated May 12, 2012.

Notice of Reasons for Rejection issued in corresponding JP 2010-528827 dated May 29, 2012.

* cited by examiner

BELTED ABSORBENT ARTICLE

TECHNICAL FIELD

The present invention provides an absorbent article comprising a belt and an absorbent structure. The absorbent structure is fastened to the belt via an article fastening means having a form and orientation such that the article fastening means does not fold or turn up under the forces present when the diaper is being worn.

BACKGROUND OF THE INVENTION

Absorbent articles such as diapers and incontinence guards are worn by incontinent persons to manage body waste such as urine or faeces. They generally comprise two important features: an absorbent structure which absorbs and manages the body waste, and components which keep the absorbent structure in place on the body of the wearer under a range of activities (e.g. walking, sitting or lying down).

Diapers and incontinence guards can be classified according to their structure. Pant diapers resemble normal underwear, and are applied to a wearer by being pulled up the wearer's legs, in the same way as regular underwear. Traditional diapers have front and rear portions which are fastened to one another around the waist of the wearer.

Belted absorbent articles, such as belt diapers, have a belt which is first fastened around the waist of a wearer. Belted absorbent articles are popular with incontinent adults as they can be changed by the wearer themselves while standing up. After fastening the belt, the absorbent structure is then brought between the legs of the wearer and fastened by article fastening means to the belt. In such articles, at least a portion of the waistband of the article only comprises the belt (i.e. the front and rear portions of the absorbent structure are not directly fastened to one another around the waist of the wearer). The present invention concerns belted absorbent articles.

Examples of belted articles are provided in WO 02/05739, WO 06/065177, WO 03/017904 and WO 03/017903.

GB 2 080 093 discloses a traditional diaper (i.e. not a belt diaper) which has strips of tape aligned in the direction of the leg elastics.

Typically, little attention has been paid to the form and/or placement of the article fastening means used to fasten the absorbent structure of a belted absorbent article to the belt. In the interests of simplicity and manufacturing efficiency, article fastening means to date have usually comprised a square or rectangle of material which is applied to the absorbent structure such that one edge is parallel to the front (longitudinal) edge or the transverse edge in the front region of the absorbent structure.

Figure 2:
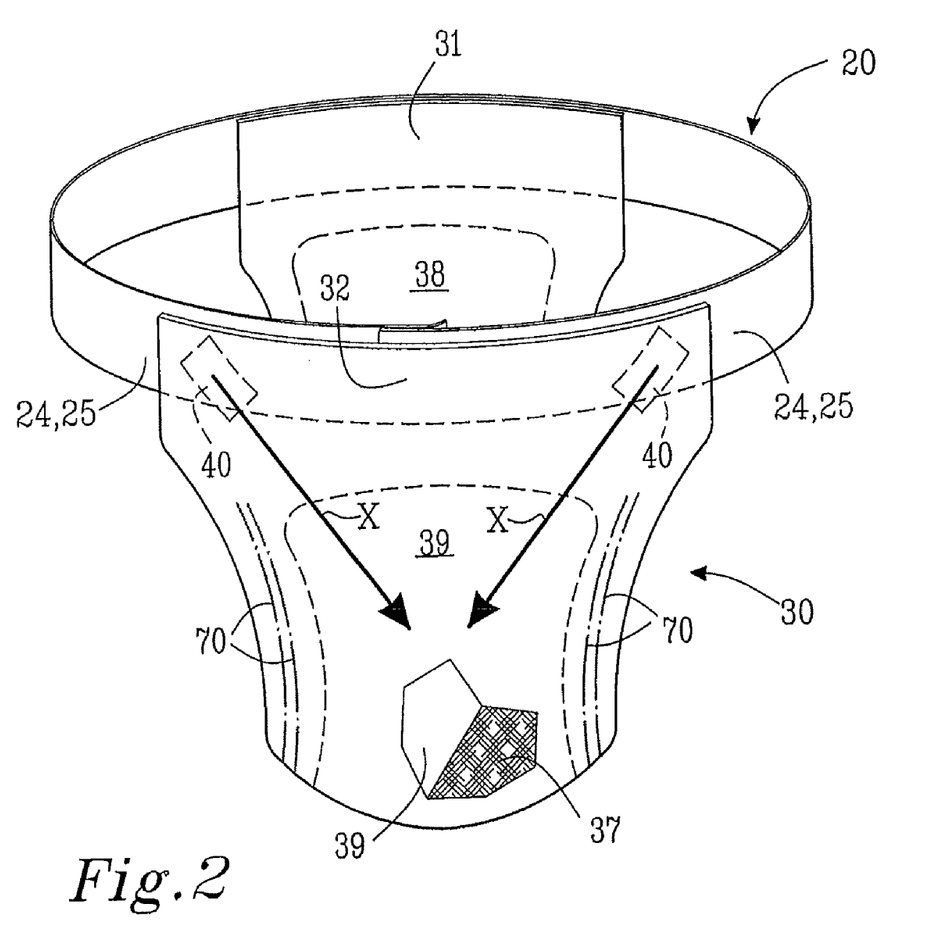
FIG. 2 shows the belt-diaper of FIG. 1 in assembled form.

However, the primary forces in the waist and hip region of such belted absorbent articles when being worn are directed from the hip region of the belt inwards and downwards towards the crotch of the wearer (see arrow X in FIG. 2). The article fastening means of the prior art are by no means ideal in such situations, and—under such forces—tend to fold upwards or be uncovered at their lower edges (see FIG. 5). This can lead to problems with poor fastening ability, as the entire article fastening means is not in full contact with the corresponding reception surface. Poor fastening in turn leads to poor fit and the risk of leakage. Furthermore, article fastening means which is exposed can fasten undesirably to the wearer's clothes or bedclothes.

There thus remains a need for a belted absorbent article in which the above problems are addressed in a simple and effective manner.

SUMMARY OF THE INVENTION

The present invention is based on the realisation that the form and alignment of the article fastening means are important for obtaining a belted absorbent article which poor fit, risk of leakage and undesirable fastening to other articles are reduced.

The invention therefore provides an absorbent article, such as a diaper or an incontinence guard. The article comprises a belt and an absorbent structure, said belt comprises an article reception surface. The absorbent structure extends in the longitudinal (L) and transverse (T) directions and has a longitudinal centre line (L1) and opposing first and second longitudinal end regions.

Each of said longitudinal end regions has a perimeter constituted by a transversely extending end edge and a pair of opposed longitudinal edges. The first longitudinal end region of said absorbent structure is attached to the belt.

The absorbent structure comprises at least one article fastening means at the second longitudinal end region thereof, said article fastening means adapted to fasten to the article reception surface on the belt such that the absorbent article adopts a pant-like shape in use. The article fastening means has a shape such that it is accommodated within an imaginary rectangle, the rectangle having opposed upper and lower first edges extending parallel to said transversely extending end edge of said second longitudinal end region and opposed distal and proximal second edges extending parallel to said pair of opposed longitudinal edges of said second longitudinal end region. A rectangle is thereby defined having an upper distal corner, an upper proximal corner, a lower distal corner and a lower proximal corner.

At least a continuous region, which is located adjacent the lower distal corner and defined by a portion of the distal second edge and a portion of the lower first edge of the imaginary rectangle, is free of article fastening means. The article fastening means contacts the imaginary rectangle at least on the lower first edge and the distal second edge thereof.

In one embodiment, an imaginary straight line drawn along at least one edge of the article fastening means towards the first longitudinal end of the absorbent structure meets the longitudinal centre line (L1) of the absorbent structure at an acute angle (α) which lies between 5° and 85°, preferably between 10° and 80°, more preferably between 15° and 45°.

Suitably, the article fastening means has a rectangular shape, a square shape, a parallelogram shape, a rhombus shape or a triangular shape in the L-T plane.

The first longitudinal end of said absorbent structure may be attached to the belt via at least one article fastening means located at the first longitudinal end of the absorbent structure, said article fastening means having the shape and alignment as described above. The first longitudinal end of the absorbent structure may be permanently attached to the belt, e.g. via glue or welding.

Suitably, the maximum extension of the article fastening means in a direction perpendicular to a force line (X) which passes through the centre of the article fastening means and which makes an angle with the longitudinal centre line (L1) of the absorbent structure of between 5° and 85°, preferably between 10° and 80°, more preferably between 15° and 45° is less than 3 cm, preferably less than 2 cm, more preferably less than 1 cm.

Preferably the belt consists of article reception surface on the garment-facing side thereof.

DEFINITIONS

The term "absorbent article" refers to products that are placed against the skin of the wearer to absorb and contain body exudates, like urine, faeces and menstrual fluid. The invention mainly concerns disposable absorbent articles, which means articles that are not intended to be laundered or otherwise restored or reused as an absorbent article after the first use.

The "absorbent structure" of the absorbent article is that component of the absorbent article which receives and stores exuded bodily fluids. As such, it comprises at least an absorbent core. The absorbent structure may be permanently attached to the belt of a belted absorbent article, or may be removably attached. Typically, the absorbent structure is manufactured before being joined to the belt of a belted absorbent article. It therefore comprises a separate component of the absorbent article to the belt.

BRIEF DESCRIPTION OF THE DRAWINGS

The invention may be more readily understood by reference to the attached drawings which, by way of example only, schematically illustrate various embodiments of the invention.

DETAILED DESCRIPTION OF PREFERRED EMBODIMENTS

Figure 1:
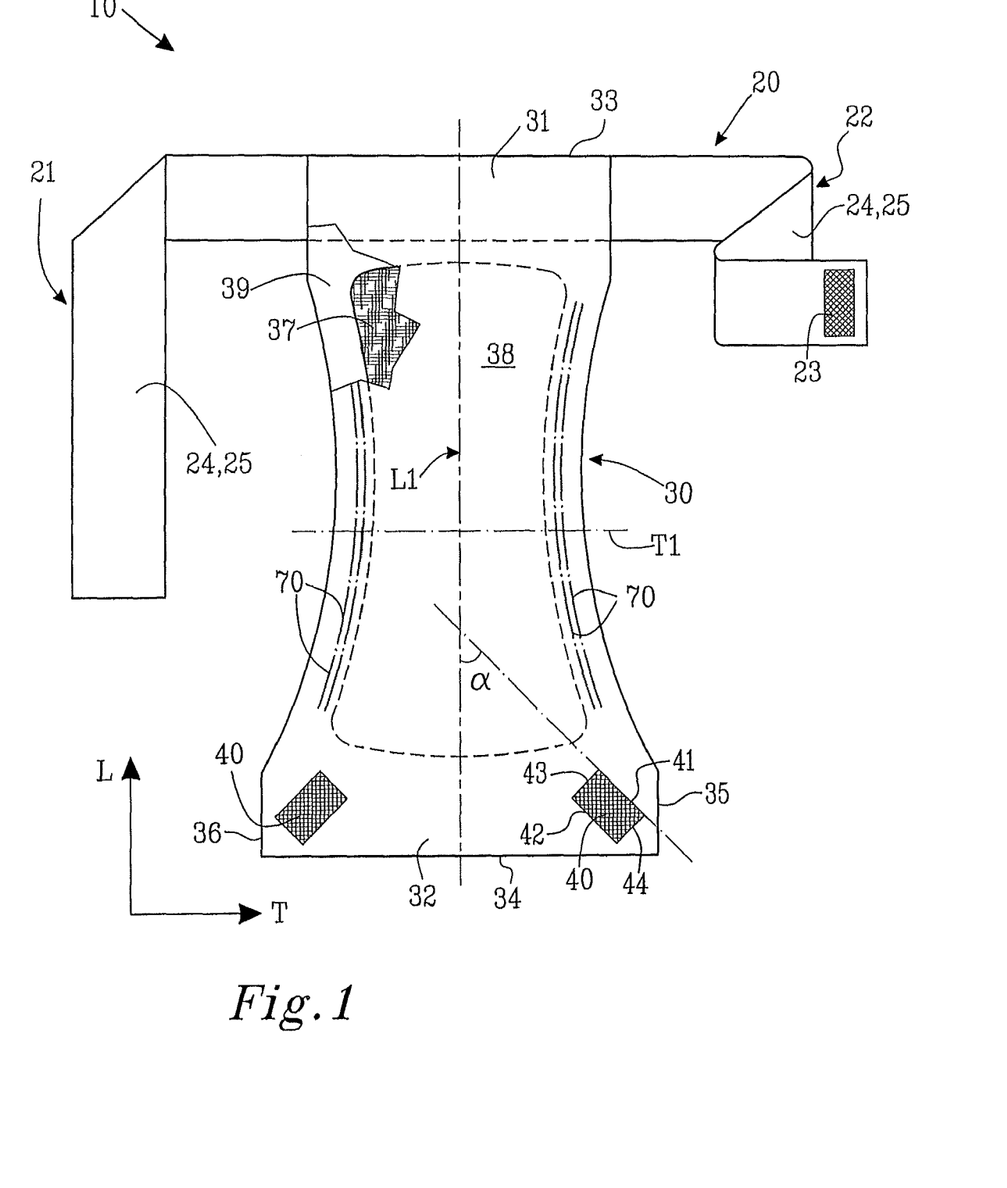
FIG. 1 shows an open belt-diaper according to the invention, seen from the wearer-facing side and with all elastic components of the absorbent structure 30 fully extended.

FIG. 1 shows an absorbent article 10 according to the invention, seen from the wearer-facing side (inside) and with all elastic components of the absorbent structure 30 fully extended. The article comprises a belt 20 and an absorbent structure 30. In FIG. 1, the belt 20 is open.

In use, the belt 20 is fastened about the wearer's waist, where it acts to hold the absorbent structure 30 in place. The belt 20 of FIG. 1 comprises two belt halves, 21, 22, although it is conceivable that a single belt is present, which wraps completely around the waist of the wearer. The belt 20 of FIG. 1 also comprises belt attachment means 23 which fastens to belt reception surface 25, so that the belt can be fastened around the waist of the wearer. If the belt attachment means 23 comprises hook material of a hook-and-loop (e.g. Velcro®) fastener, belt reception surface 25 suitably comprises loop material. Likewise, if the belt attachment means 23 comprises adhesive material, the belt reception surface 25 suitably comprises a plastic film material to which the adhesive material can fasten, preferably in a releasable manner. The belt 20 may comprise a single length of belt material, to which the absorbent structure 30 is attached, or may comprise two separate lengths of belt material, each of which is attached to the absorbent structure 30.

The width of the belt 20 should be between circa 50 mm and 250 mm. The belt 20 may comprise nonwoven material or plastic film, or laminates thereof. In a preferred embodiment, the belt 20 comprises a laminate of at least one nonwoven material and at least one plastic film. The belt 20 may have elastic properties in at least one region thereof, and in at least one direction, preferably in the length direction of the belt. Elastic properties may be provided by the use of one or more elastic components, such as e.g. elastic threads, elastic nonwoven materials or elastic films. Belts 20 having elastic properties are particularly useful. The belt 20 is desirably breathable, and the material constituting the belt 20 may be perforated or porous or the belt 20 may be spaced from the skin of the wearer by spacer fabric or spacer elements.

The belt 20 comprises an article reception surface 24, which is preferably the same material as belt reception surface 25. Indeed, a single reception surface (e.g. of nonwoven material) may constitute both the article reception surface 24 and the belt reception surface 25. The article reception surface 24 is located on the outside (garment-facing) surface of the belt 20 when worn. Article reception surface 24 and belt reception surface 25 may each comprise separate pieces of material which are joined to the belt 20 during manufacture, or the wearer-facing surface of the belt 20 may itself consist of one or both of these reception surfaces 24, 25 (as shown in FIG. 1).

The absorbent structure 30 is the component of the absorbent article 10 which receives and stores exuded bodily fluids. It extends in the longitudinal (L) and transverse (T) directions as shown in FIG. 1, and may have any suitable shape, e.g. rectangular, hourglass or T-shaped. In use, the absorbent structure 30 is located between the legs of the wearer so as to cover the wearer's genitals and anal region, and is held in place on the wearer by the belt 20. The absorbent structure 30 has a longitudinal centre line (L1) about which it is symmetrical, and opposing first 31 and second 32 longitudinal end regions. Each of said longitudinal end regions 31, 32 has a perimeter constituted by a transversely extending end edge 33, 34 and a pair of opposed longitudinal edges 35, 36.

Traditionally, belt diapers are applied to a wearer by fastening the belt 20 around the wearer's waist, with the absorbent structure 30 hanging downwards at the wearer's rear. The absorbent structure 30 is then brought between the wearer's legs and fastened to the belt 20 at the wearer's front. In this case, the first longitudinal end region 31 of the absorbent structure 30 will comprise the rear portion of the absorbent article 10, while the second longitudinal end region 32 of the absorbent structure 30 will comprise the front portion of the absorbent article 10. However, the reverse situation is also possible.

In cross-section, the absorbent structure 30 usually comprises a liquid-permeable topsheet 38, a liquid-impermeable backsheet 39 and an absorbent core 37 located between said topsheet 38 and said backsheet 39. However, in certain absorbent structures 30, it may be sufficient to include only an absorbent core 37 and a liquid-impermeable backsheet 39.

The topsheet 38 of the absorbent structure 30 is the layer which lies in contact with the wearer's body when the absorbent article is in use. As such, it should be soft, non-irritating and comfortable against the skin, and bodily fluid should be able to pass through it without hindrance. The topsheet 38 can consist of a nonwoven material, e.g. spunbond, meltblown, carded, hydroentangled, wetlaid etc. Suitable nonwoven materials can be composed of natural fibers, such as wood-pulp or cotton fibres, manmade fibres, such as polyester, polyethylene, polypropylene, viscose etc. or from a mixture of natural and manmade fibres. The topsheet may further be composed of tow fibres, which may be bonded to each other in a bonding pattern, as e.g. disclosed in EP-A-1 035 818. Further examples of materials suitable for topsheets are porous foams, apertured plastic films etc. The topsheet 38 may be different in different parts of the absorbent structure 30.

The backsheet 39 of the absorbent structure 30 is the layer which lies furthest from the wearer's body when the article is in use. To protect the wearer's garments from soiling, it should be liquid-impermeable, but is desirably gas-permeable to allow air and vapour to pass in and out of the article so that the warm, damp conditions which can arise in a diaper are reduced. Typically, the backsheet 39 is of a liquid impervious material, such as a thin plastic film, e.g. a polyethylene or polypropylene film, a nonwoven material coated with a liquid impervious material, a hydrophobic nonwoven material, which resists liquid penetration or a laminate comprising plastic films and nonwoven materials. Examples of breathable backsheet materials are porous polymeric films, nonwoven laminates of spunbond and meltblown layers and laminates of porous polymeric films and nonwoven materials. The backsheet 39 may be different in different parts of the absorbent structure 30.

The absorbent core 37 of the absorbent structure 30 acts to receive and contain liquid and other bodily exudates and can be of any conventional kind. As such, it typically comprises absorbent material. Examples of commonly-occurring absorbent materials are cellulosic fluff pulp, tissue layers, highly-absorbent polymers (so called superabsorbents), absorbent foam materials, absorbent nonwoven materials or the like. It is common to combine cellulosic fluff pulp with superabsorbents in an absorbent body. It is also common to have absorbent cores comprising layers of different material with different properties with respect to liquid receiving capacity, liquid distribution capacity and storage capacity. The thin absorbent cores, which are common in for example baby diapers and incontinence guards, often comprise a compressed mixed or layered structure of cellulosic fluff pulp and superabsorbent material. The size and absorbent capacity of the absorbent core 16 may be varied to be suited for different uses such as for infants or for incontinent adults.

The absorbent core 37 may comprise one or more layers which are designed to improve the handling of bodily waste. Such layers are designed to receive a large amount of liquid in a short space of time and distribute it evenly across the absorbent structure 30. They may include so-called transfer, distribution, surge or acquisition layers, and are usually located between the topsheet 38 and the absorbent core 37.

The topsheet 38 and backsheet 39 generally have a similar extension in the plane of the article, while the absorbent core 37 has an extension which is somewhat smaller. The topsheet 38 and backsheet 39 are joined to one another around the periphery of the absorbent core 37, so that the core 37 is enclosed within the envelope formed by the topsheet 38 and the backsheet 39. The absorbent core 37 is at least located in the crotch portion of the absorbent article 10, and may also extend somewhat into the front and rear portions. The topsheet 38, backsheet 39 and other components of the absorbent article 10 may be joined to one another by any means common in the art, e.g. ultrasonic welding, thermal welding or gluing.

In addition, the absorbent structure 30 may comprise one or more elastic elements 70. These help the article 10 fit tightly against the body of the wearer, and are usually present as leg or waist elastic elements (shown as leg elastic elements 70 in FIG. 1).

The first longitudinal end region 31 of said absorbent structure 30 is attached to the belt 20. Attachment of the absorbent structure 30 to the belt 20 may occur substantially in the middle of the belt, as shown in FIG. 1, or towards one end of the belt 20. The attachment may be permanent—i.e. it is not possible to separate the first longitudinal end region 31 of the belt 20 without tearing or otherwise damaging the article 10. Alternatively, the first longitudinal end region 31 of the absorbent structure 30 may be removably attached to the belt 20 via at least one article fastening means 40' located at the first longitudinal end region 31 of the absorbent structure 30, said article fastening means 40' having the shape and alignment of the article fastening means 40 as described herein.

The absorbent structure 30 comprises at least one (e.g. two) article fastening means 40 at the second longitudinal end region 32 thereof. Preferably, the absorbent structure comprises two article fastening means 40 at the second longitudinal end region 32, each of which is located towards the transverse edge thereof. The article fastening means 40 is adapted to fasten to the article reception surface 24 on the belt 20 such that the absorbent article 10 adopts a pant-like shape in use (FIG. 2). As such, it may comprise a hook portion of a hook-and-loop type fastener (e.g. Velcro®), or an adhesive tab.

The present invention is based on the discovery that the form and alignment of the article fastening means 40 are significant for obtaining a secure fit and for minimizing the risk of the fastening means being undesirably uncovered or turned up. As mentioned above, the primary forces in the waist and hip region of belted absorbent articles when being worn are directed from the hip region of the belt inwards and downwards towards the crotch of the wearer (see arrow X in FIG. 2). The angle $\alpha$ made between the longitudinal centre line of the article and the force arrow X typically lies between 5° and 85°, preferably between 10° and 80°, more preferably between 15° and 45°.

The article fastening means 40 of the invention has a shape such that it is accommodated within an imaginary rectangle 50. The imaginary rectangle comprises a rectangular area located towards the transverse edge of the second longitudinal end region 32; i.e. in that region where the article fastening means 40 is located. The article fastening means 40 is totally enclosed within the imaginary rectangle. The maximum extension of the article fastening means 40 in the transverse and longitudinal directions corresponds to the maximum extension of the imaginary rectangle 50 in the transverse and longitudinal directions.

Figure 3:
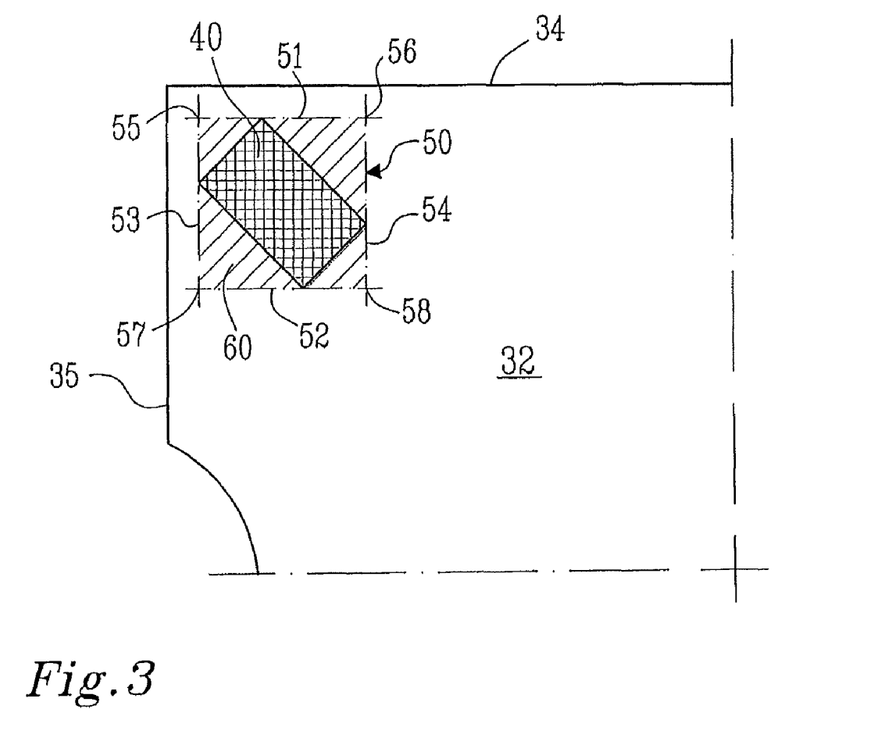
FIG. 3 shows a close-up of the second longitudinal end region of the article.

As shown in FIG. 3, the rectangle 50 has opposed upper and lower first edges 51, 52 extending parallel to said transversely extending end edge 34 of the second longitudinal end region 32. It also has opposed distal and proximal second edges 53, 54 extending parallel to said pair of opposed longitudinal edges 35, 36 of said second longitudinal end region 32. A rectangle 50 is thereby defined which has an upper distal corner 55, an upper proximal corner 56, a lower distal corner 57 and a lower proximal corner 58, the edges of which are aligned with the longitudinal/transverse directions.

As used herein, the terms "upper" and "lower" are used to refer to a component or an element (such as the edge of the rectangle 50) which lies further away from (=upper) or closer to (=lower) the transversely-extending centre line T1 of the absorbent structure 30, relative to another component or element.

Similarly, the term "distal" and "proximal" are used to refer to a component or element which is further from (=distal) or closer to (=proximal) the longitudinal centre line than another component or element.

The article fastening means 40 contacting said imaginary rectangle 50 at least two places. The article fastening means 40 may contact the imaginary rectangle 50 at two places if the article fastening means has a parallelogram shape in the L-T plane. The article fastening means 40 may contact said imaginary rectangle 50 at three places if it has a triangle shape in the L-T plane. The article fastening means 40 may contact said imaginary rectangle 50 at four places if it has a square or rectangular shape in the L-T plane.

A continuous region 60 is located adjacent the lower distal corner 57 of the imaginary rectangle 50. The continuous region 60 is defined by a portion of the distal second edge 53 and a portion of the lower first edge 52 of the imaginary rectangle 50, and the edge of the article fastening means 40 which lies closest to the lower distal corner 57. By "a portion of" a given edge is meant that the continuous region 60 is not defined by the entire length of said edge. At least this continuous region 60 is free of article fastening means 40.

The article fastening means 40 of the invention maximises the extension of the article fastening means 40 which lies along the force line (X), while minimising the extension of the article fastening means 40 in the region outside this line, particularly in the lower distal corner 57 of the imaginary rectangle. In addition, the article fastening means 40 of the invention avoids the presence of sharp (acute) angles in the region outside the force line (X). These features reduce the tendency for the article fastening means 40 to turn up or become uncovered in use.

Preferably, one place at which the article fastening means 40 contacts the imaginary rectangle 50 is located on the lower first edge 52. In this way, good alignment of the article fastening means 40 with the force arrow X can be obtained.

Figure 4A:
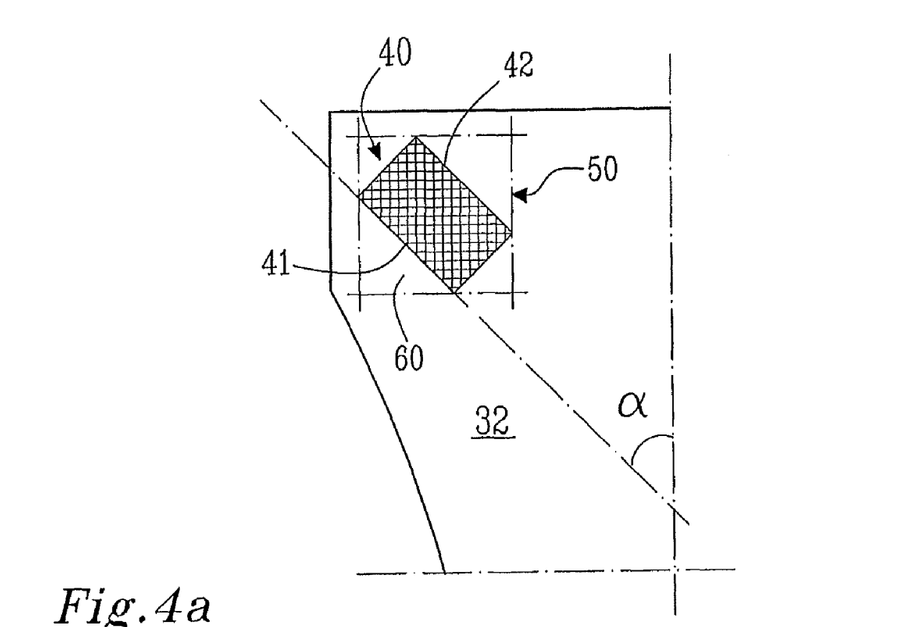
FIGS. 4a-e show alternatives for the article fastening means 40.
Figure 4B:
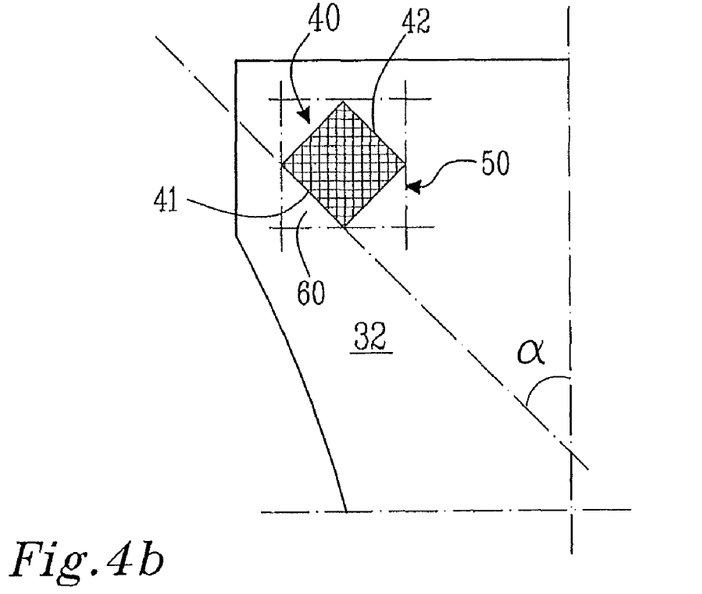

An imaginary straight line drawn along at least one edge of the article fastening means 40 towards the first longitudinal end 31 of the absorbent structure 30 preferably meets the longitudinal centre line L1 of the absorbent structure at an acute angle α which lies between 5° and 85°, preferably between 10° and 80°, more preferably between 15° and 45° (see FIGS. 4a, 4b).

Figure 4C:
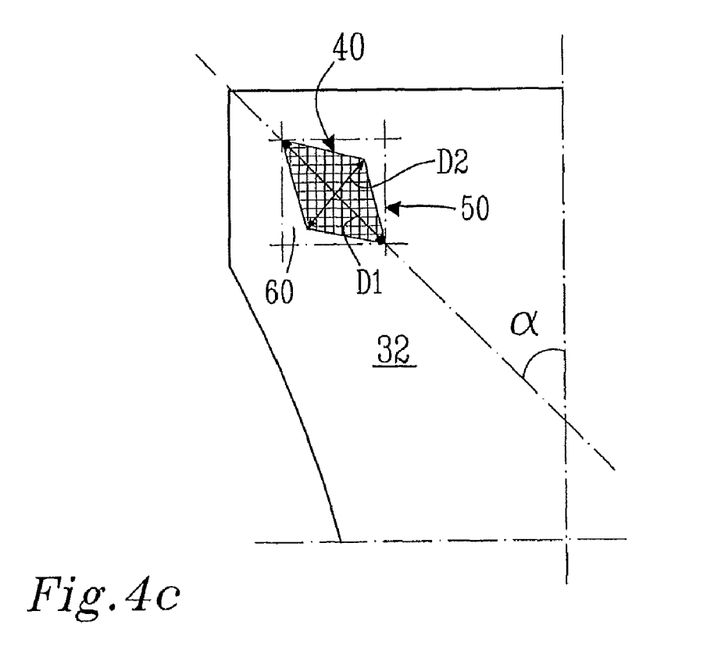

Alternatively, an imaginary straight line drawn as a continuation of a diagonal of the article fastening means 40 towards the first longitudinal end 31 of the absorbent structure 30 preferably meets the longitudinal centre line L1 of the absorbent structure at an acute angle α which lies between 5° and 85°, preferably between 10° and 80°, more preferably between 15° and 45° (see e.g. FIG. 4c).

Figure 4D:
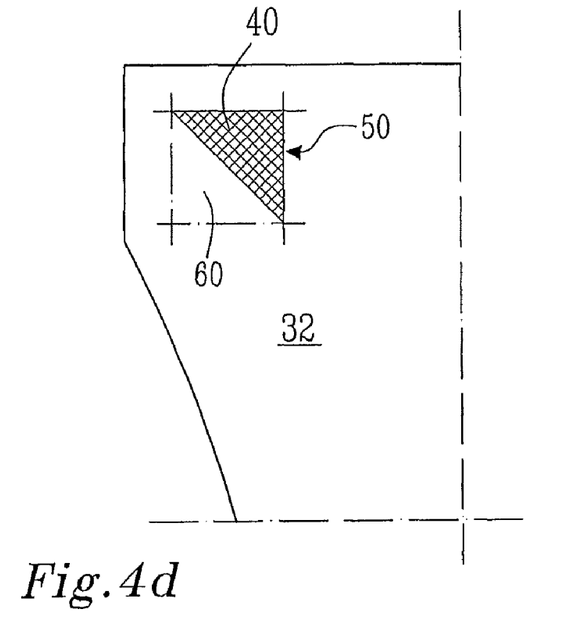
Figure 4E:
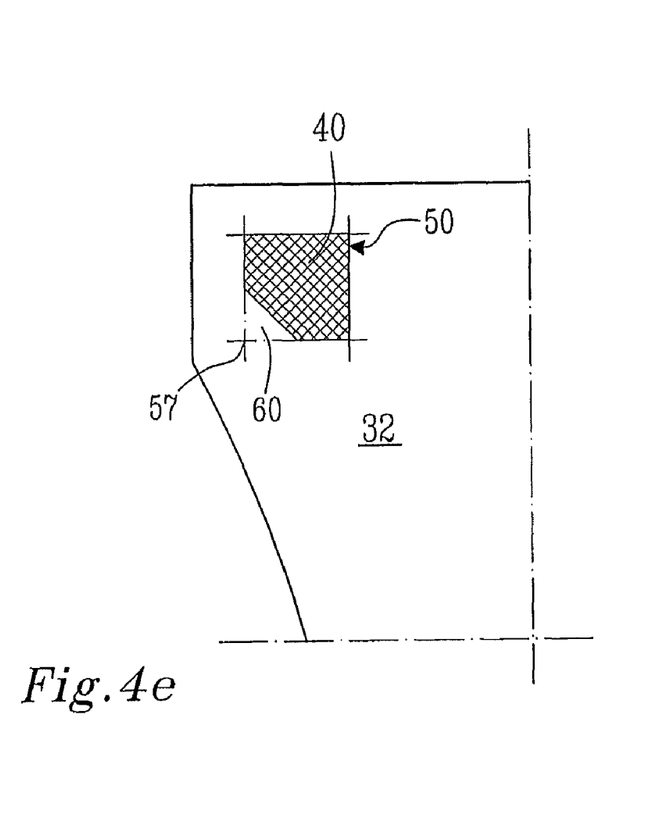

The article fastening means 40 of the invention may have a rectangular shape (FIG. 4a), a square shape (FIG. 4b), a parallelogram shape, a rhombus shape or a triangular shape (FIG. 4d) in the L-T plane. Of these, rectangular, square, parallelogram and rhombus shapes are most preferred, as they can be easily produced from a strip of fastening means with little or no wasted material. FIG. 4e shows an article fastening means 40 which is based on a square, in which the material in the lower distal corner 57 is absent. Suitably, the article fastening means 40 is not circular or ellipse-shaped.

Suitably, the maximum extension of the article fastening means 40 in a direction perpendicular to a force line (X) which passes through the centre of the article fastening means 40 and which makes an angle with the longitudinal centre line (L1) of the absorbent structure 30 of between 5° and 85°, preferably between 10° and 80°, more preferably between 15° and 45°, is less than 3 cm, preferably less than 2 cm, more preferably less than 1 cm.

Figure 5:
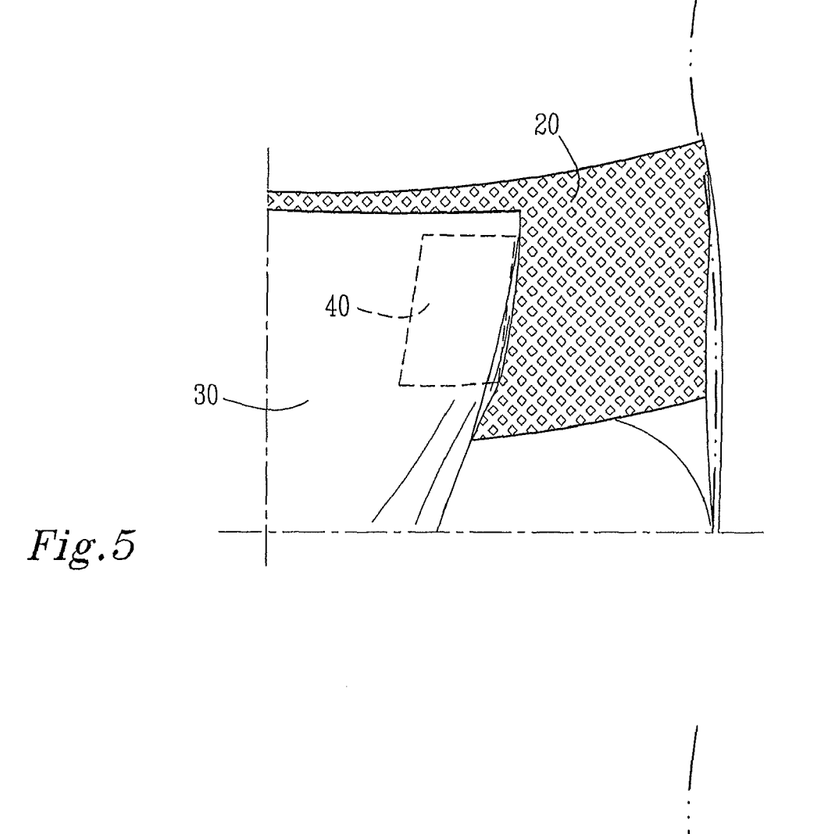
FIG. 5 is an illustration of an absorbent fastening means of the invention.

FIG. 5 is an illustration of an absorbent article 10 according to the invention in the fastened configuration, magnified in the region around the absorbent structure where it fastens to the belt. The article fastening means 40 in this case has a parallelogram shape. As can be seen in FIG. 5, the entire article fastening means 40 lies flat against the belt, without being undesirably turned up or exposed.

Figure 6:
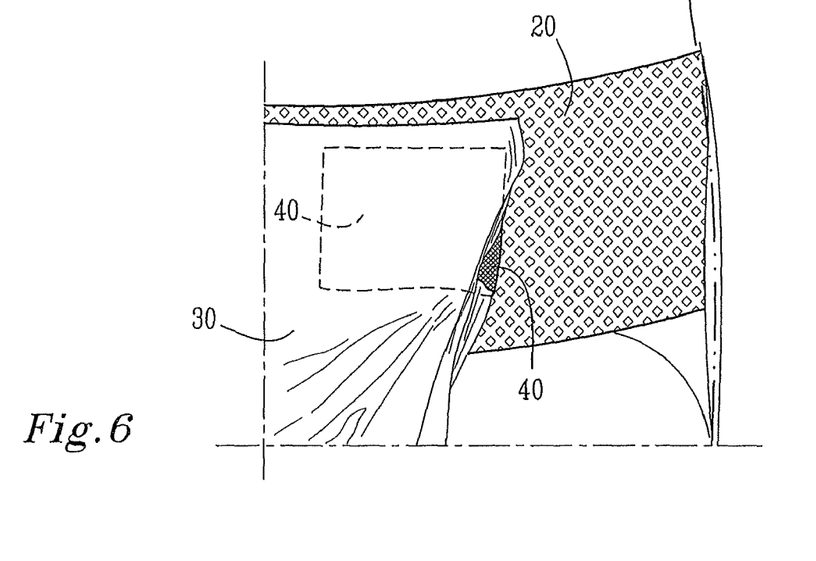
FIG. 6 is an illustration of an absorbent fastening means of the prior art.

FIG. 6 is an illustration of a prior art absorbent article in the fastened configuration, magnified in the region around the absorbent structure where it fastens to the belt. The article fastening means is a simple rectangle, the edges of which are parallel to the edges of the absorbent structure. It is evident how the force line in the absorbent structure causes the article fastening means to turn up at its lower right-hand edge, thus exposing the article fastening means 40.

The invention has been described with reference to a number of embodiments and accompanying Figures. However, the full scope of the invention is determined by the appended claims.

The invention claimed is:

1. An absorbent article comprising:
   a belt and an absorbent structure;
   said belt comprising an article reception surface and a transversely extending edge;
   said absorbent structure extending in a longitudinal direction and a transverse direction and having a longitudinal center line and opposing first and second longitudinal end regions;
   each of said longitudinal end regions having a perimeter constituted by a transversely extending end edge and a pair of opposed longitudinal edges,
   said first longitudinal end region of said absorbent structure being attached to the belt so that the transversely extending edge of the belt and the transversely extending edge end of the absorbent structure are arranged to be substantially parallel;
   said absorbent structure comprising at least one article fastener at the second longitudinal end region thereof, said article fastener adapted to fasten to the article reception surface on the belt such that the absorbent article adopts a pant shape when worn;
   said article fastener having a shape such that it is accommodated within an imaginary rectangle, the rectangle having opposed upper and lower first edges extending parallel to said transversely extending end edge of said second longitudinal end region and opposed distal and proximal second edges extending parallel to said pair of opposed longitudinal edges of said second longitudinal end region to thereby define the rectangle having an upper distal corner, an upper proximal corner, a lower distal corner and a lower proximal corner;
   at least a continuous region, which is located adjacent the lower distal corner and defined by a portion of the distal second edge and a portion of the lower first edge of the imaginary rectangle, is free of the article fastener;
   the article fastener contacts the imaginary rectangle at least on the lower first edge and the distal second edge thereof; and
   wherein a maximum extension of the article fastener in a direction perpendicular to a force line which passes through a center of the article fastener and which makes an angle with the longitudinal center line of the absorbent structure of between 5° and 80° is less than 3 cm.

2. The absorbent article according to claim 1, wherein an imaginary straight line drawn along at least one edge of the article fastener towards the first longitudinal end of the absorbent structure meets the longitudinal center line of the absorbent structure at an acute angle which lies between 5° and 85°.

3. The absorbent article according to 2, wherein the article fastener has a rectangular shape or a square shape, a parallelogram shape or a rhombus shape in a plane of the absorbent structure.

4. The absorbent article according to claim 1, wherein the article fastener has a rectangular shape, a square shape, a parallelogram shape, a rhombus shape, or a triangular shape in a plane of the absorbent structure.

5. The absorbent article according to claim 1, wherein the first longitudinal end of said absorbent structure is attached to the belt via at least one second article fastener located at the first longitudinal end of the absorbent structure, said second article fastener having the shape and alignment as defined in claim 1.

6. The absorbent article according to claim 1, wherein the first longitudinal end of said absorbent structure is permanently attached to the belt.

7. The absorbent article according to claim 1, wherein the belt consists of an article reception surface on a garment-facing side thereof.

8. The absorbent article according to claim 1, wherein an imaginary straight line drawn along at least one edge of the article fastener towards the first longitudinal end of the absorbent structure meets the longitudinal center line of the absorbent structure at an acute angle which lies between 10° and 80°.

9. The absorbent article according to claim 1, wherein an imaginary straight line drawn along at least one edge of the article fastener towards the first longitudinal end of the absorbent structure meets the longitudinal center line of the absorbent structure at an acute angle which lies between 15° and 45°.

10. The absorbent article according to claim 1, wherein the maximum extension of the article fastener in a direction perpendicular to a force line which passes through a center of the article fastener and which makes an angle with the longitudinal center line of the absorbent structure of between 10° and 80° is less than 3 cm.

11. The absorbent article according to claim 10, wherein the maximum extension of the article fastener in a direction perpendicular to a force line which passes through a center of the article fastener and which makes an angle with the longitudinal center line of the absorbent structure of between 10° and 80° is less than 2 cm.

12. The absorbent article according to claim 10, wherein the maximum extension of the article fastener in a direction perpendicular to a force line which passes through a center of the article fastener and which makes an angle with the longitudinal center line of the absorbent structure of between 10° and 80° is less than 1 cm.

13. The absorbent article according to claim 1, wherein the maximum extension of the article fastener in a direction perpendicular to a force line which passes through a center of the article fastener and which makes an angle with the longitudinal center line of the absorbent structure of between 15° and 45° is less than 3 cm.

14. The absorbent article according to claim 13, wherein the maximum extension of the article fastener in a direction perpendicular to a force line which passes through a center of the article fastener and which makes an angle with the longitudinal center line of the absorbent structure of between 15° and 45° is less than 2 cm.

15. The absorbent article according to claim 13, wherein the maximum extension of the article fastener in a direction perpendicular to a force line which passes through a center of the article fastener and which makes an angle with the longitudinal center line of the absorbent structure of between 15° and 45° is less than 1 cm.

\* \* \* \* \*